United States Patent [19]
Giudicelli et al.

[11] 3,953,449
[45] Apr. 27, 1976

[54] 2-(4-M-CF$_3$ OR -SCF$_3$ PHENYLPIPERAZINO)-ETHYL BENZOATES

[75] Inventors: Don Pierre Rene Lucien Giudicelli, Fontenay-sous-Bois; Henry Najer; Bogdan Iliesco-Branceni, both of Paris; Philippe Michel Jacques Manoury, L'Hay-les-Roses; Andre Pierre Fernand Dumas, Bagneux, all of France

[73] Assignee: Synthelabo, Paris, France

[22] Filed: May 6, 1974

[21] Appl. No.: 467,595

[30] Foreign Application Priority Data
May 9, 1973 France .............................. 73.16634
Jan. 29, 1974 France .............................. 74.02793

[52] U.S. Cl. ........................ 260/268 PH; 424/250; 424/232
[51] Int. Cl.$^2$ ...................................... C07D 295/08
[58] Field of Search .............................. 260/268 PH

[56] References Cited
UNITED STATES PATENTS 3,557,107  1/1971  Cinnamon et al. .......... 260/268 PH
3,846,430  11/1974  de Antoni .................... 260/268 PH FOREIGN PATENTS OR APPLICATIONS
889,223  2/1962  United Kingdom OTHER PUBLICATIONS
Miles Laboratories, Inc. Chemical Abstracts Vol. 57, p. 13778h.

Primary Examiner—Alton D. Rollins
Assistant Examiner—Jose Tovar
Attorney, Agent, or Firm—Armstrong, Nikaido & Wegner

[57] ABSTRACT

The invention provides compound of formula

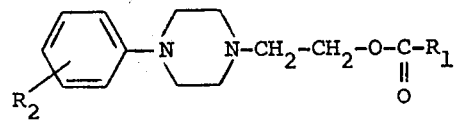

wherein R$_1$ is alkyl or substituted or unsubstituted phenyl or 3-pyridyl, and R$_2$ is hydrogen, halogen, alkoxy or trifluoromethyl, methoxy or methylthio. The compounds are useful as analgesic agents.

8 Claims, No Drawings

2-(4-M-CF$_3$ OR -SCF$_3$ PHENYLPIPERAZINO)-ETHYL BENZOATES

This invention relates to certain arylpiperazinoalkanol esters and their addition salts with pharmaceutically acceptable inorganic and organic acids, to pharmaceutical compositions containing them and to a method of treating mammals using them.

The present invention provides compounds of general formula (I):

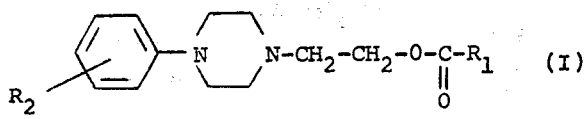

wherein
  $R_1$ is an alkyl of 1 to 10 carbon atoms; a phenyl which is unsubstituted or substituted by one to three substituents, which may be the same or different and which is a halogen, a hydroxy, acetoxy, amino or alkoxy of 1 to 5 carbon atoms,

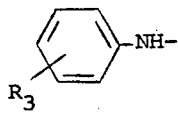

wherein
  $R_3$ is a hydrogen or halogen, or a trifluoromethyl, trifluoromethoxy or trifluoromethylthio; or

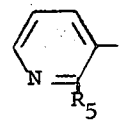

wherein
  $R_5$ is a hydrogen or halogen or $R_5$ is

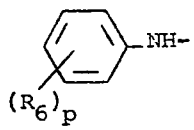

wherein
  $p$ is an integer of 0 to 2 and each $R_6$, which may be the same or different, is a halogen, an alkyl of 1 to 3 carbon atoms or a trifluoromethyl, trifluoromethoxy or trifluoromethylthio; and
  $R_2$ is a hydrogen or halogen, an alkoxy of 1 to 3 carbon atoms or a trifluoromethyl, trifluoromethoxy or trifluoromethylthio; or an acid addition salt thereof with a pharmaceutically acceptable organic or inorganic acid.

The compounds of the invention are suitable for use as pharmaceuticals for use in human and veterinary therapy, especially as analgesic agents.

They can be prepared by using known methods, and especially by means of the following processes:

In a general process, which can be used to prepare any compound of general formula (I), an acid of formula $R_1$—$CO_2H$ wherein $R_1$ is as defind above, or one of its functional derivatives, which is preferably a halide, an anhydride or an ester, is reacted, preferably under heating, with a piperazinoalkanol of formula

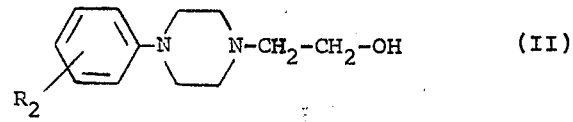

wherein $R_2$ and $n$ are as defined above under conditions which are those most favourable for the acid derivative chosen.

Thus, for example, an acid halide, and particularly a chloride, and a compound of general formula (II) are reacted at the reflux temperature of an apolar solvent such as an aromatic hydrocarbon, e.g. benzene, toluene or xylene; or chloroform; in this case, the presence of a tertiary base which accepts the hydrogen halide acid can be advantageous;

an acid anhydride and a compound of general formula (II), are heated at 80° to 150°C; in this case, the presence of a solvent is not absolutely necessary; An ester, $R_1$—$COOR_9$, wherein $R_9$ represents a lower alkyl group, such as methyl, ethyl or propyl, and a compound of general formula (II) are reacted at the reflux temperature of an apolar solvent such as an aromatic hydrocarbon. A transesterification reaction, which is often promoted by the presence of an alkali metal, for example sodium, takes place.

With the derivatives of 2-aminonicotinic acid (I; $R_1$ = [pyridine structure with $R_5$])

it is also possible to react a halogenated ester of formula:

[structure showing pyridine-C(O)-O-CH$_2$-CH$_2$-N(piperazine)N-phenyl-$R_2$ with X on pyridine]

(X being a halogen, especially chlorine) with an amine of formula

[H$_2$N-phenyl-$(R_6)_p$ structure]

at the reflux temperature of a polar solvent such as an alcohol, a glycol or a alkoxyalkanol, for example 2-methoxyethanol. This process is illustrated in Example 9 below.

In the case of derivatives of anthranilic acid

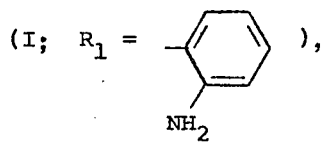

it is also possible to carry out the reaction in accordance with one of the following reaction schemes:

Scheme 1

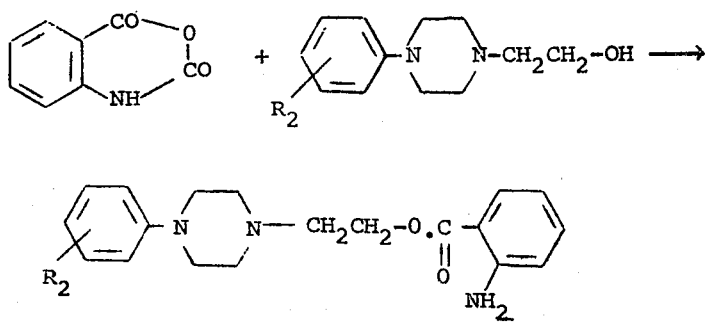

The reaction is preferably carried out at the reflux temperature of an apolar solvent, especially an aromatic hydrocarbon like benzene, toluene or xylene. This process is illustrated by Examples 13 to 15 below.

Scheme 2

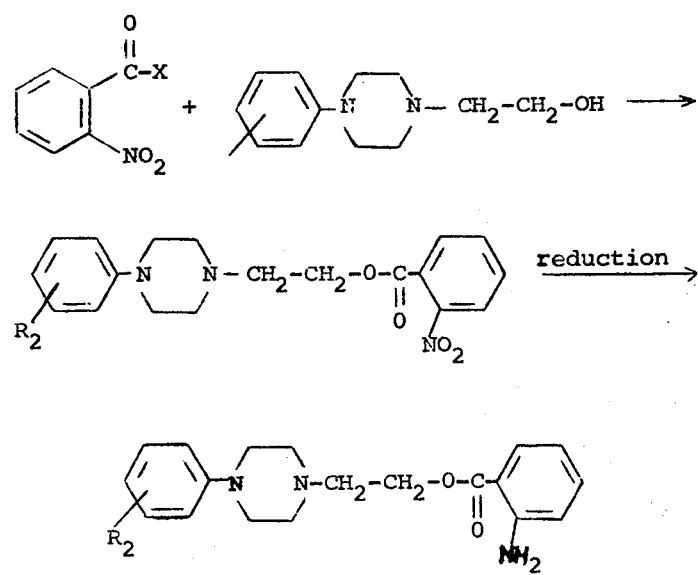

The condensation step is carried out in an apolar solvent such as chloroform, working firstly under cold conditions (−20° to +20°) and then heating gradually to 50°–80° in order to complete the reaction.

The subsequent reduction step is carried out catalytically or chemically, and especially by hydrogenation in the presence of palladium on charcoal. This process is illustrated by Example 18 below.

The present invention also provides a process for preparing a compound of general formula

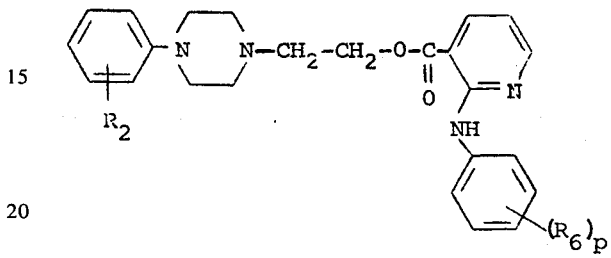

which process comprises reacting a compound of general formula (II) with a 2-halonicotinic acid or a functional derivative thereof and reacting the resulting nicotinate with an amine of general formula

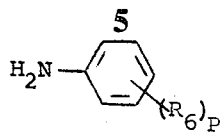

and a process for preparing a compound of general formula

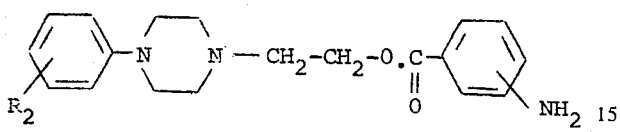

which process comprises reacting a compound of formula (II) with a nitrobenzoic acid or a functional derivative thereof, and hydrogenating the resulting nitrobenzoate.

In the description of the foregoing processes, $n$, $R_1$, $R_2$ and $R_6$ have the meanings given in the definition of the compounds of the general formula (I).

The invention also provides a pharmaceutical composition comprising, as the active ingredient, a compound of general formula (I), and a pharmaceutically acceptable carrier or diluent. The compositions can be those suitable for administration, orally, endorectally or parenterally.

For oral administration, any pharmaceutical form suited to this method can be used; examples are tablets, dragees, gelatin-coated pills, capsules, cachets, solutions or potable suspensions. The unit dose of the compound can vary between 10 and 500 mg, and the daily dose between 50 and 2,000 mg.

For rectal administration, suppositories containing 20 to 500 mg. of the compound are used and are administered to the patient at the rate of one to four per 24 hours.

For parenteral administration, injectable solutions, buffered to the physiological pH and prepared in advance or at the time of use, are employed. The unit dose is between 10 and 500 mg. and the maximum daily dose is 1,000 mg.

The invention is illustrated by the following Examples.

EXAMPLE 1

2-(4-m-Trifluoromethylphenylpiperazino)-ethyl acetate and its monohydrochloride ($R_1 = CH_3$; $R_2 = 3—CF_3$; Code No.: SL B 093)

2 Drops of acetyl chloride are added to 12 g (0.0437 mol) of 2-(4-m-trifluoromethylphenylpiperazino)-ethanol in 100 ml of acetic anhydride and the mixture is heated at 100° for 1 hour. The excess acetic anhydride is evaporated under reduced pressure to give a residue which is dissolved in ether. The ethereal solution is washed with water and then with sodium bicarbonate solution; it is dried over anhydrous magnesium sulphate and the solvent is driven off. An oily product is obtained which is distilled under reduced pressure to give 11.5 g (yield: 82.2%) of 2-(4-m-trifluoromethylphenyl-piperazino)-ethyl acetate, which distils at 185°C under a pressure of 0.01 mm of mercury.

Analysis: $C_{15}H_{19}F_3N_2O_2$; molecular weight: 316.325 calculated: C,56.95; H,6.05; N,8.85%. found: C,57.07; H,5.93; N,8.90%.

To prepare the hydrochloride, 15.8 g (0.05 mol) of the above base are dissolved in 100 ml of methylene chloride, and 12.5 ml (0.05 mol) of 4 N-hydrogen chloride in ethanol are added. The solvents are evaporated and the salt is recrystalised from 2-propanol to give 15.6 g (yield: 88.5%) of 2-(4-m-trifluoromethylphenylpiperazino)-ethyl acetate monohydrochloride, which melts at 170°C.

Analysis: $C_{15}H_{20}ClF_3N_2O_2$; molecular weight = 352.786 Calculated C,51.06; H,5.71; N,7.98; Cl,10.04%. Found: C,51.11; H,5.73; N,7.97; Cl, 9.86%.

EXAMPLE 2

2-(4-m-Trifluoromethylthiophenylpiperazino)-ethyl acetate and its monohydrochloride. ($R_1 = CH_3$; $R_2 = 3—SCF_3$; Code No.: SL B 157).

Following the procedure of Example 1 but using 10 g (0.0326 mol) of 2-(4-m-trifluoromethylthiophenylpiperazino)-ethanol and 60 ml of acetic anhydride, 9.55 g (yield: 84%) of 2-(4-m-trifluoromethylthiophenylpiperazino)-ethyl acetate, which distils at 145°–150°C under a pressure of 0.01 mm of mercury, are obtained.

Analysis: $C_{15}H_{19}F_3N_2O_2S$; molecular weight = 348.389 Calculated: C,51,71; H,5.47; N,8.04%. Found: C,51.84; H,5.41; N,8.10%.

The monohydrochloride is prepared by dissolving 9.55 g (0.0274 mol) of the above base in 70 ml of 2-propanol and adding 6.85 ml of N-hydrogen chloride in ethanol. The salt formed is filtered off and dried in vacuo to give 8.5 g (yield: 80.4%) of 2-(4-m-trifluoromethylthiophenyl-piperazino)-ethyl acetate monohydrochloride, which melts at 114°C.

Analysis: $C_{15}H_{20}ClF_3N_2O_2S$; molecular weight = 384.850 Calculated: C,46.81; H,5.23; N,7.27; Cl⁻,9.21%. Found: C,46.77, 46.84; H,5.42, 5.23; N,7.51, 7.51; Cl⁻,9.47, 9.40%.

EXAMPLE 3

2-(4-m-Trifluoromethylphenylpiperazino)-ethyl 5-chloro-2-methoxy-benzoate and its monohydrochloride ($R_1 = 2—$methoxy-5-chlorophenyl; $R = 3—CF_3$; Code No. SL B 165)

9.1 G. (0.033 mol) of 2-(4-m-trifluoromethylphenylpiperazino)-ethanol and 6.7 g. (0.066 mol) of triethylamine are dissolved in 80 ml. of anhydrous benzene. This solution is refluxed and 6.9 g. (0.033 mol) of 5-chloro-2-methoxy-benzoyl chloride in 80 ml. of benzene are added dropwise with stirring. Refluxing and stirring are continued for 3 hours after the end of the addition. The mixture is cooled, triethylamine hydrochloride is filtered off, and the filtrate is washed with water. The organic phase is dried over magnesium sulphate, and the solvent is evaporated. The oily residue is dissolved in ether and a slight excess of hydrogen chloride in ether is added to the solution. The salt which has precipitated is filtered off and recrystallised from ethanol to give 10.2 g. (yield: 65%) of 2-(4-m-trifluoromethylphenyl-piperazino)-ethyl-5-chloro-2-methoxy-benzoate monohydrochloride, which melts at 190°C.

Analysis: $C_{21}H_{23}Cl_2F_3N_2O_3$; molecular weight = 479.329 Calculated: C, 52,51; H, 5.03; N, 5.83; total Cl, 14.76%. Found: C, 52.53; 52.39; H, 5.08, 5.10; N, 5.71, 5.84; total Cl, 14.59, 14.65%.

EXAMPLE 4

2-(4-m-Trifluoromethylphenylpiperazino)-ethyl benzoate ($R_1 = C_6H_5$; $R_2 = 3-CF_3$; Code No. SLB 108)

15 G. (0.054 mol) of 2-(4-m-trifluoromethylphenyl-piperazino)-ethanol, 14 g. (0.103 mol) of methyl benzoate and 125 ml. of dry toluene are introduced into a distillation apparatus. The reaction mixture is refluxed to drive off azeotropically any traces of water which may be present therein, 0.06 g. of sodium is then added, and slow distillation of the methanol formed during the reaction is continued. When the reaction is complete, the reaction mixture is filtered while hot to remove a little insoluble matter, the toluene is evaporated from the filtrate, the gummy residue is triturated in petroleum ether to convert it to a fine powder, and the powder is filtered off, dried in vacuo and recrystallised from isopropyl alcohol to give 17.2 g. (yield: 84%) of 2-(4-m-trifluoromethylphenyl-piperazino)-ethyl benzoate, which melts at 95°C.

Analysis: $C_{20}H_{21}F_3N_2O_2$; molecular weight: 378.397 Calculated: C, 63.48; H, 5.59; N, 7.40%. Found: C, 63.54; H, 5.71; N, 7.32%.

EXAMPLE 5

2-(4-m-Trifluoromethylphenylpiperazino)-ethyl 3,4,5-trimethoxybenzoate and its monohydrochloride ($R_1 = 3,4,5$-trimethoxybenzoate; $R_2 = 3-CF_3$; Code No. SLB 169)

The procedure of Example 4 is followed, but 5.4 g. (0.02 mol) of 2-(4-m-trifluoromethylphenyl-piperazino)-ethanol, 4.5 g. (0.02 mol) of methyl 3,4,5-trimethoxybenzoate, 80 ml. of toluene and 0.02 g. of sodium are used. Reaction is complete after 8 hours of heating and slow distillation. The toluene is evaporated, the oily residue is dissolved in ether, the ethereal solution is washed with water and dried over magnesum sulphate, and the ether is driven off to give 9.2 g. (yield: 97.8%) of 2-(4-m-trifluoromethyl-phenylpiperazino)-ethyl 3,4,5-trimethoxy-benzoate as an oil.

The above base is dissolved in isopropyl alcohol and the calculated amount of hydrogen chloride in ether is added. The salt which has precipitated is filtered off and recrystallised from 2-propanol to give 7.1 g. (yield: 72%) of 2-(4-m-trifluoromethylphenylpiperazino)-ethyl 3,4,5-trimethoxybenzoate hydrochloride, which melts at 198°C.

Analysis: $C_{23}H_{28}ClF_3N_2O_5$; molecular weight: 504.94 Calculated: C, 5.71; H, 5.59; F, 11.29; Cl⁻, 7.02%. Found: C, 54.68; H, 5.48; F, 11.11; Cl⁻, 6.99, 6.98%.

EXAMPLE 6

2-(4-m-Trifluoromethylphenyl-piperazino)-ethyl 2-n-propyl-pentanoate and its dihydrochloride. [$R_1 = (CH_3CH_2CH_2)_2CH-$; $R_2 = 3-CF_3$; Code No.: SL B 198]

Following the procedure of Example 4, 10.32 g (0.06 mol) of ethyl 2-n-propylpentanoate, 16.44 g (0.06 mol) of 2-(4-m-trifluoromethylphenylpiperazino)-ethanol, 200 ml of toluene and 0.03 g of sodium are used. After heating for 8 hours, the toluene is evaporated and the remaining product is dissolved in ether. The organic solution is washed with water and dried over magnesium sulphate, and the ether is evaporated. The oily residue is rectified under reduced pressure to give 14.4 g (yield: 60%) of 2-(4-m-trifluoromethylphenyl-piperazino)-ethyl 2-n-propyl-pentanoate, which distils at 172°–174°C under a pressure of 0.1 mm of mercury.

To prepare the dihydrochloride, the above base (0.036 mol) is dissolved in acetone ether (60:40) and 18 ml (0.072 mol) of 4 N-hydrogen chloride in ether are added gradually with stirring. The salt which has precipitated is filtered off, wahsed with ether and dried. To purify it, it is dissolved in boiling acetone, the hot solution is filtered to remove insoluble matter and half its volume of ether is added to the filtrate to give 12 g. (yield: 70.5%) of 2-(4-m-trifluoromethylphenyl-piperazino)-ethyl 2-n-propyl-pentanoate dihydrochloride, which melts at 140°C.

Analysis: $C_{21}H_{33}Cl_2F_3N_2O_2$; molecular weight: 473.41 Calculated: C, 53.28; H, 7.02; Cl⁻, 14.97%. Found: C, 53.00, 52.98; H, 6.99, 6.99; Cl⁻, 15.11, 15.15%.

EXAMPLE 7

2-(4-m-Chlorophenylpiperazino)-ethyl 2-m-trifluoromethyl-thioanilinobenzoate and its monohydrochloride ($R_1 = $ 2-m-trifluoromethylthioanilinophenyl; $R_2 = 3$-Cl; Code No. SLB 146)

11.4 G. (0.035 mol) of methyl 2-m-trifluoromethyl-thioanilino-benzoate, 9.63 g. (0.04 mol) of 2-(4-m-chloro-phenylpiperazino)-ethanol, 150 ml. of dry toluene and 0.06 g. of sodium are introduced into a distillation apparatus. This mixture is refluxed and the methanol which formed is distilled slowly for 6 hours. The remaining toluene is evaporated to give an oily product which is purified by chromatography on a silica column, eluting with methylene chloride/acetone (90:10). The fractions containing the pure product are combined and the solvents are evaporated to give 17.5 g. (yield: 93.2%) of 2-(4-m-chlorophenylpiperazino)-ethyl 2-m-trifluoromethyl-thioanilinobenzoate as an oil.

17.48 G. (0.0326 mol) of the above base are dissolved in 150 ml. of methylene chloride and 8.15 ml (0.0326 mol) of 4-N-hydrogen chloride in ethanol are added with stirring. The solvent is evaporated and the remaining product crystallised from ethanol to give 12.6 g (yield: 67.7%) of 2-(4-m-chlorophenyl-piperazino)-ethyl 2-m-trifluoromethylthioanilinobenzoate monohydrochloride, which melts at 200°C.

Analysis: $C_{26}H_{26}Cl_2F_3N_3O_2S$; molecular weight: 572.481 Calculated: C, 54.55; H, 4.58; N, 7.34; total Cl, 12.38%. Found: C, 54.41, 54.43; H, 4.78, 4.63; N, 7.16, 7.22; total Cl, 12.32, 12.45%.

EXAMPLE 8

2-(4-m-Trifluoromethylphenylpiperazino)-ethyl 2-chloronicotinate and its monohydrochloride. ($R_1 = $ 2-chloro-3-pyridyl; $R_2 = 3-CF_3$;)

A solution of 27.5 g (0.1 mol) of 2-(4-m-trifluoromethylphenyl-piperazino)-ethanol in 100 ml of chloroform is cooled to −5°C, and 8.8 g (0.055 mol) of 2-chloro-nicotinoyl chloride in 50 ml of chloroform are introduced dropwise with stirring over 30 minutes. The reaction mixture is allowed to return to ambient temperature and stirring is continued for 1 hour. The 2-(4-m-trifluoro-methylphenyl-piperazino)-ethanol hydrochloride which precipitated is filtered off, and the chloroform solution is washed with sodium bicarbonate solution and is dried over magnesium sulphate. The solvent is driven off to give 19.6 g (yield: 86.3%) of 2-(4-m-trifluoromethylphenyl-piperazino)-ethyl 2-chloronicotinate as an oil.

19G.(0.046 mol) of the above amino-ester are dissolved in methylene chloride and 11.5 ml (0.046 mol) of 4 N-hydrogen chloride in ethanol are added. The solvents are evaporated and the residue is crystallised from isopropyl alcohol to give 16.1 g. (yield: 77.8%) of 2-(4-m-trifluoromethylphenylpiperazino)-ethyl 2-chloronicotinate monohydrochloride, which melts at 182°C.

Analysis: $C_{19}H_{20}Cl_2F_3N_3O_2$; molecular weight = 450.291 Calculated: C, 50.68; H, 4.47; N, 9.33; Cl$^-$, 7.87% Found: C, 50.55, 50.51; H, 4.68, 4.66; N, 9.28; Cl$^-$, 8.03, 8.04%.

EXAMPLE 9

2-(4-m-Trifluoromethylphenylpiperazino)-ethyl 2-(3-chloro-2-methylanilino)-nicotinate ($R_1$ = 2-(3-chloro-2-methylanilino)-3-pyridyl; $R_2$ = 3—$CF_3$; Code No. SLB 152)

A mixture of 4.5 g. (0.01 mol) of 2-(4-m-trifluoromethylphenylpiperazino)-ethyl 2-chloronicotinate monohydrochloride, prepared in Example 10, 2.83 g. (0.02 mol) of 3-chloro-2-methylaniline and 30 ml. of 2-methoxy-ethanol is refluxed. After heating for 1 hour, the mixture is acidified with hydrogen chloride in ethanol until the pH is 2 to 3, and then heating is continued for 7 hours. The solvents are evaporated to obtain the crude hydrochloride. The base is liberated therefrom by treating it with aqueous sodium bicarbonate. The mixture is extracted with ether, the organic solution is washed and dried and the ether is evaporated. The amino-ester obtained is purified by chromatography on a silica column, eluting with methylene chloride/acetone (90:10). The fractions containing the pure product are combined, the solvents are driven off, and the residue is crystallised from 2-propanol to give 2.5 g. (yield: 48%) of 2-(4-m-trifluoromethylphenylpiperazino)-ethyl 2-(3-chloro-2-methylanilino)-nicotinate, which melts at 91°C. Analysis: $C_{26}H_{26}ClF_3N_4O_2$; molecular weight = 518.971 Calculated: C, 60.17; H, 5.05; N, 10.79%. Found: C, 59.94, 60.00; H, 5.10, 5.04; N, 10.60, 10.64%.

EXAMPLE 10

2-(4-p-Methoxyphenylpiperazino)-ethyl-2-m-trifluoromethyl-anilino-benzoate and its monohydrochloride ($R_1$ = 2-m-trifluoro-methylanilinophenyl; $R_2$ = 4—$OCH_3$; n = 2; Code No. SLA 224)

11.615 G. (0.05 mol) of 2-(4-p-methoxyphenyl-piperazino)-ethanol, 13.918 g.(0.045 mol) of ethyl 2-m-trifluoromethylanilino-benzoate, 0.6 g. of sodium and 100 ml. of toluene are refluxed in a distillation flask equipped with a magnetic stirrer. Distillation is carried out slowly for 5 hours, driving off the ethanol formed in the reaction. The reaction mixture is filtered while hot and the toluene is evaporated from the filtrate. The remaining product is dissolved in ether, and the ethereal solution is washed several times with water and dried over anhydrous magnesium sulphate. The solvent is driven off and the solid residue is recrystallised from isopropyl alcohol to give 16.2 g. (yield: 72.2%) of 2-(4-p-methoxyphenylpiperazino)-ethyl 2-m-trifluoromethylanilinobenzoate, which melts at 78°C.

The hydrochloride is prepared by dissolving 10 g. (0.02 mol) of the above amino-ester in 60 ml. of methylene chloride, and 5 ml. of 4 N-hydrogen chloride in ethanol are added. The solvents are evaporated and the salt is recrystallised from ethanol to give 9.65 g. (yield: 90%) of 2-(4-p-methoxyphenylpiperazino)-ethyl 2-(m-trifluoromethylanilino)-benzoate monohydrochloride, which melts at 182°C.

Analysis: $C_{27}H_{29}F_3ClN_3O_3$; molecular weight = 535.998 Calculated: C, 60.50; H, 5.45; N, 7.83; Cl$^-$, 6.61%. Found: C, 60.36; H, 5.50; N, 7.72; Cl$^-$, 6.66%.

EXAMPLE 11

2-(4-m-Trifluoromethylphenylpiperazino)-ethyl salicylate ($R_1$ = o-hydroxyphenyl; $R_2$ = 3—$CF_3$; Code No. SLB 262)

13.75 G. (0.05 mol) of 2-(4-m-trifluoromethylphenyl-piperazino)-ethanol, 7 g. (0.07 mol) of methyl salicylate, 0.20 g. of sodium and 150 ml. of dry toluene are refluxed. Heating is continued for 6 hours while slowly driving off the methanol formed during the reaction. The mixture is filtered while hot and the toluene is evaporated to give an oil which is dissolved in methylene chloride. The organic solution is washed with water and dried over magnesium sulphate, the solvent is driven off and the residue is recrystallised twice from isopropyl alcohol to give 12.75 g. (yield 65.2%) of 2-(4-m-trifluoromethylphenylpiperazino)-ethyl salicylate, which melts at 61°C.

Analysis: $C_{20}H_{21}F_3N_2O_3$; molecular weight = 394.406 Calculated: C, 60.90; H, 5.36; N, 7.10%. Found: C, 60.95, 60.77; H, 5.47, 5.50; N, 7.14%.

EXAMPLE 12

2-(4-m-Trifluoromethylphenylpiperazino)-ethyl 2-acetoxy-benzoate and its monohydrochloride ($R_1$ = 2-acetoxyphenyl; $R_2$ = 3—$CF_3$; Code No. SLB 258)

A solution of 36.6 g. (0.134 mol) of 2-(4-m-trifluoromethylphenylpiperazino)-ethanol in 300 ml. of dry chloroform is cooled to −10°C, and, at this temperature, 14 g. (0.07 mol) of 2-acetoxy-benzoyl chloride are added in small portions with stirring. The reaction mixture is allowed to return to ambient temperature and stirring is continued for 3 hours. The hydrochloride of the aminoalcohol is filtered off and the chloroform solution is washed with sodium bicarbonate solution and then with water. It is dried, the solvent is evaporated, and the residual product is purified by chromatography on a silica column, eluting with methylene chloride/acetone (9:1). The fractions containing the pure product (checked by thin layer chromatography) are combined and the solvents are driven off to give 17.6 g. (yield: 57.7%) of 2-(4-m-trifluoromethyl-phenylpiperazino)-ethyl 2-acetoxybenzoate as an oil.

The above amino-ester is dissolved in isopropyl alcohol and 9 ml. (0.036 mol) of 4 N-hydrogen chloride in ethanol are added. The solvents are evaporated and the salt obtained is recrystallised from isopropyl alcohol to give 14.1 g. (yield: 82.9%) of 2-(4-m-trifluoromethyl-phenylpiperazino)-ethyl 2-acetoxy-benzoate monohydrochloride, which melts at 170°C.

Analysis: $C_{22}H_{24}ClF_3N_2O_4$; molecular weight = 472.895 Calculated: C, 55.87; H, 5.12; N, 5.92; Cl$^-$, 7.49%. Found: C, 55.86, 55.79; H, 5.13; N, 5.99, 5.87; Cl$^-$, 7.67%.

EXAMPLE 13

2-(4-m-Trifluoromethylphenylpiperazino)-ethyl anthranilate ($R_1$ = 2-aminophenyl; $R_2$ = 3—$CF_3$; Code No. SLB 109)

22 G. (0.08 mol) of 2-(4'-m-trifluoromethylphenyl-piperazino)-ethanol and 17.5 g. (0.107 mol) of isatoic anhydride in 200 ml. of toluene is refluxed for 3 hours, the reaction being followed by thin layer chromatography [eluant: $CH_2CL_2$/acetone (9:1)]. The hot solution is treated with a little animal charcoal and then filtered, and the toluene is evaporated from the filtrate to give a residue which is taken up in ether. A little insoluble isatoic anhydride is filtered off, the ether is driven off and the remaining product is triturated in petroleum ether in order to suspend it; it is filtered off and recrystallised from isopropyl alcohol to give 23 g. (yield = 73.2%) of 2-(4-m-trifluoromethylphenylpiperazino)-ethyl anthranilate, which melts at 73°C.

Analysis: $C_{20}H_{22}F_3N_3O_2$ (393.41) Calculated: C, 61.06; H, 5.63; N, 10.68%. Found: C, 61.21; H, 5.70; N, 10.68%.

EXAMPLE 14

2-(4-m-Chlorophenylpiperazino)-ethyl anthranilate ($R_1$ = 2-aminophenyl; $R_2$ = 3—Cl; Code No. SLB 113)

7.2 G. (0.03 mol) of 2-(4-m-chlorophenyl-piperazino)-ethanol and 6.55 g. (0.04 mol) of isatoic anhydride in 125 ml. of toluene are refluxed for 3 hours. The hot toluene solution is filtered and the toluene is evaporated from the filtrate to give a residue which is taken up in ether in order to remove a small amount of unreacted isatoic anhydride, the solution is filtered and the ether is driven off. The remaining product is triturated in petroleum ether, filtered off and recrystallised twice from isopropyl alcohol to give 7.6 g. (yield = 70%) of 2-(4-m-chlorophenylpiperazino)-ethyl anthranilate, which melts at 76°C.

Analysis: $C_{13}H_{22}ClN_3O_2$ (359.86) Calculated: C, 63.41; H, 6.16; N, 11.67; Cl, 9.85%. Found: C, 63.67; H, 6.32; N, 11.59; Cl, 9.11%.

EXAMPLE 15

2-(4-m-Trifluoromethylthiophenyl-piperazino)-ethylanthranilate ($R_1$ = 2-aminophenyl; $R_2$ = 3—$SCF_3$; n = 2; Code No. SLB 114)

5.7 G. (0.0186 mol) of 2-(4-m-trifluoromethyl-thiophenylpiperazino)-ethanol and 3.3 g. (0.021 mol) of isatoic anhydride in 100 ml. of toluene are refluxed for 3 hours. A little animal charcoal is added, the hot toluene solution is filtered, and the filtrate is evaporated to dryness to give a residue which is taken up in ether, a small amount of isatoic anhydride is filtered off and then the ether is driven off. The residue is triturated in petroleum ether, filtered and recrystallised from isopropyl alcohol to give 6.2 g. (yield = 78%) of 2-(4-m-trifluoro-methylthiophenylpiperazino)-ethyl anthranilate, which melts at 83°C.

Analysis: $C_{20}H_{22}F_3N_3O_2S$ (425.48) Calculated: C, 56.46; H, 5.21; N, 9.87%. Calculated with 1.4% of water (measured by the Karl Fischer method): C, 55.67; H, 5.35; N, 9.73%. Found: C, 55.28, 55.31; H, 5.09, 5.16; N, 9.62, 9.56%.

EXAMPLE 16

2-(4-m-Chlorophenylpiperazino)-ethyl anthranilate ($R_1$ = 2-aminophenyl; $R_2$ = 3—Cl; Code No. SLB 113)

10.6 G. (0.07 mol) of methyl anthranilate, 12.1 g (0.05 mol) of 2-(4-m-chlorophenylpiperazino)-ethanol, 150 ml. of dry toluene and 0.09 g. of sodium are heated in a distillation apparatus for 2 ½ hours on an oil bath, while slowly distilling the methanol eliminated in the transesterification reaction. The toluene solution is filtered while hot to remove a small amount of insoluble matter, the toluene is evaporated from the filtrate, and the residue is triturated in petroleum ether, filtered and recrystallised from isopropyl alcohol to give 13 g. (yield = 72%) of 2-(4-m-chlorophenyl-piperazino)-ethyl anthranilate, which melts at 77°C., and which is found to be identical to the product prepared in Example 18 using a mixed melting point.

Analysis: $C_{13}H_{22}ClN_3O_2$ (359.86) Calculated: C, 63.41; H, 6.16; N, 11.67%. Found: C, 63.51, 63.45; H, 6.37, 6.20; N, 11.31, 11.65%.

EXAMPLE 17

2-(4-m-Trifluoromethylphenylpiperazino)-ethyl anthranilate ($R_1$ = 2-aminophenyl; $R_2$ = 3—$CF_3$; Code No. SLB 109)

Following the procedure of Example 16, 33.6 g. (0.122 mol) of 2-(4-m-trifluoromethylphenyl-piperazino)ethanol, 22 g. (0.146 mol) of methyl anthranilate and 0.1 g. of sodium in 150 ml. of toluene are reacted, while distilling slowly in order to remove the methanol formed during the reaction. After heating for 2 hours, the toluene solution is filtered while hot, and the solvent is evaporated to give a residue which is triturated in petroleum ether, filtered and recrystallised from isopropyl alcohol to give 36.5 g. (yield = 76%) of 2-(4-m-trifluoromethylphenyl-piperazino)-ethyl anthranilate, which melts at 74° and which was shown to be identical with the product obtained in Example 13 using a mixed melting point.

Analysis: $C_{20}H_{22}F_3N_3O_2$ (393.41) Calculated: C, 61.06; H, 5.63; N, 10.68%. Found: C, 60.90; H, 5.74; N, 10.66%.

EXAMPLE 18

2-(4-m-Chlorophenylpiperazino)-ethyl anthranilate ($R_1$ = 2-aminophenyl; $R_2$ = 3—Cl; Code No. SLB 113)

A. 3.9 G. (0.021 mol) of 2-nitrobenzoyl chloride in 20 ml. of chloroform are added dropwise, with stirring, to 5 g. (0.021 mol) of 2-(4-m-chlorophenyl-piperazino)- ethanol in 30 ml. of chloroform, the latter solution having been cooled to −10°. The temperature is kept between −5° and 10° for the entire duration of the addition, and is then allowed to return to that of the laboratory. The reaction is completed by heating for 2 hours at 60° with stirring. The mixture is cooled, the aminoester hydrochloride which has precipitated is filtered off and suspended in methylene chloride, and saturated sodium bicarbonate is added with stirring to liberate the base. The organic layer is washed with water, dried over sodium sulphate and filtered, the solvent is driven off from the filtrate, and the remaining product is recrystallised twice from isopropyl alcohol to give 6.1 g. (yield = 74.8) of 2-(4-m-chlorophenyl-piperazino)-ethyl 2-nitro-benzoate, which melts at 58°.

Analysis: $C_{19}H_{20}ClN_3O_4$ (389.84) Calculated: C, 58.53; H, 5.17; N, 10.77; Cl, 9.09%. Found: C, 58.33, 58.30; H, 5.30, 5.21; N, 10.80; Cl, 9.36%.

B. 5.75 G. (0.015 mol) of 2-(4-m-chlorophenyl-piperazino)-ethyl 2-nitrobenzoate in 100 ml. of methanol is hydrogenated at ambient temperature and at atmospheric pressure, in the presence of 1 g. of 10% palladium on charcoal. The theoretical amount of hydrogen (1 l.) is absorbed in 40 minutes. The catalyst is filtered off, the methanol is evaporated from the filtrate, and the residue is recrystallised from isopropyl alcohol to give 4 g. (yield = 74.1%) of 2-(4-m-chloro-phenylpiperazino)-ethyl anthranilate, which melts at 77° and which was shown to be identical, using a mixed melting point, to the product of Examples 14 and 16.

EXAMPLE 19

The compounds shown in Table I below were prepared using the techniques of the above Examples.

TABLE I

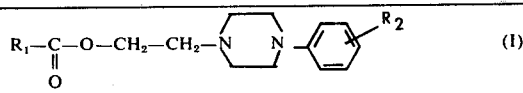
(I)

| Code No. | $R_1$ | $R_2$ (in the 3-position) | Yield % | Physical constants | Calculated % C | H | N | Cl | F | Found % C | H | N | Cl | F |
|---|---|---|---|---|---|---|---|---|---|---|---|---|---|---|
| SL B 238 | H N—⌬— | $CF_3$ | Base 26 | Base M.p. = 129.5° | 61.06 | 5.63 | 10.68 | | | 60.68 | 5.56 | 10.49 | | |
| SL B 210 | ⌬(N)— | $CF_3$ | HCl 60 | HCl m.p. =220° | 54.87 | 5.09 | 10.10 | 8.52 | | 54.89 54.94 | 5.17 5.21 | 10.09 | 8.71 8.67 | |
| SL B 145 | pyridyl-NH—⌬—$SCF_3$ | Cl | HCl 77 | HCl m.p. =220° | 52.36 | 4.39 | 9.77 | 12.36 | | 51.13 52.26 | 4.44 | 9.66 9.74 | 12.49 | |
| SL B 147 | ⌬—NH—⌬—$SCF_3$ | $CF_3$ | HCl 83 | HCl m.p. =212° | 53.51 | 4.32 | 6.93 | 5.85 | | 53.59 53.44 | 4.39 4.37 | 6.86 6.78 | | 6.03 5.92 |
| SL B 148 | pyridyl-NH—⌬—$SCF_3$ | $CF_3$ | HCl 59 | HCl m.p. =224° | 51.44 | 4.15 | 9.23 | 5.84 | | 51.55 51.43 | 4.42 4.46 | 9.25 | | 5.95 6.11 |
| SL B 149 | ⌬—NH—⌬—$CF_3$ | $CF_3$ | HCl 58 | HCl m.p. =188° | 56.50 | 4.57 | 7.32 | 6.18 | | 56.40 56.38 | 4.83 4.92 | 7.34 7.28 | | 6.39 6.08 |
| SL B 279 | ⌬—NH—⌬—$CF_3$ | H | Base 58 HCl 80 | Base m.p. =65° HCl m.p. =186° | 61.72 | 5.38 | 8.30 | 6.95 | 11.26 | 61.88 | 5.31 | 8.07 8.24 | 6.96 | 11.20 11.17 |

TABLE I-continued

| Code No. | $R_1$ | $R_2$ (in the 3-position) | Yield % | Physical constants | Calculated % C | H | N | Cl | F | Found % C | H | N | Cl | F |
|---|---|---|---|---|---|---|---|---|---|---|---|---|---|---|
| SL B 260 | (2-OCOCH$_3$-phenyl) | H | Base 49.5 | Base m.p. = 60° | 68.46 | 6.56 | 7.60 | | | 68.26 / 68.25 | 6.55 / 6.56 | 7.64 / 7.48 | | |
| | | | HCl 86.9 | HCl m.p. =150° | 62.29 | 6.22 | 6.91 | 8.75 | | 62.23 / 62.201 | 6.37 / 6.42 | 6.91 / 6.93 | 9.04 / 9.04 | |

The compounds of the invention were subjected to pharmacological tests which demonstrated their valuable propertis, especially as analgesic agens. Table II gives the results obtained with the representative compounds, SLB 093, SLB 108, SLB 169 and SLB 198, and with amidopyrine chosen as the reference substance.

Acute toxicity

The tests were carried out on Swiss mice of the CD1 strain, of both sexes, and the 50% lethal doses (LD$_{50}$) were calculated graphically.

Analgesic effect

The analgesic effect was investigated in accordance with two conventional experimental procedures.

a. Effect against pain induced in CD1 mice by the intraperitoneal injection of acetic acid, in accordance with the technique described by Koster et al (Fed. Proc. 1959, 18, 42) and modified by Peterfalvi, et al. (Med. Pharmacol. exp., 1966, 15 254).

b. Test using a plate heated by acetone vapour carried out on CD1 mice in accordance with the method of Eddy and Leimbach (J. Pharmacol. exp. Therap., 1953, 107, 386).

The results show that the compounds of the invention, in addition to being markedly less toxic than the reference substance, possess an analgesic activity which is much greater than that of the latter in both the tests carried out, which demonstrate, on the one hand, analgesic effects with preponderantly peripheral action (Koester test) and, on the other hand, analgesic effects with a preponderantly central nervous action (heated plate test). The therapeutic ratio of the compounds of the invention is considerable.

TABLE II

| Compound | Acute toxicity oral administration LD$_{50}$ mg/kg | Analgesic activity oral administration mg/kg Koster test ED$_{50}$ (1) | Heated plate MAD (2) |
|---|---|---|---|
| SLB 093 (Example 1) | 925 | 3.5 | 15 |
| SLB 108 (Example 4) | >4,000 | 10 | 25 |
| SLB 169 (Example 5) | 2,200 | 15 | 30 |
| SLB 198 (Example 6) | 2,200 | 4.3 | 10 |
| Amidopyrine | 850 | 40 | 175 |

(1) 50% effective dose
(2) Mean active dose

The compounds of the invention can thus be used in human and veterinary medicine, in the treatment of various pain syndromes.

I claim:

1. A compound of the formula

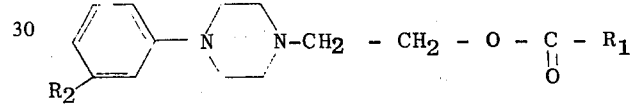

$R_1$ is phenyl, 2-methoxy-5-chloro phenyl, 3,4,5-trimethoxyphenol, 2-hydroxyphenyl, 2-acetoxyphenyl, 2- or 4-amino-phenyl, 2-(m-trifluoromethyl-phenylamino)-phenyl or 2-(m-trifluoromethylthio-phenylamino)-phenyl; and
   $R_2$ is CF$_3$ or SCF$_3$ or an acid addition salt thereof with a pharmaceutically acceptable organic or inorganic acid.

2. A compound as claimed in claim 1, which is 2-(4-m-trifluoromethylphenylpiperazino)-ethyl benzoate.

3. A compound as claimed in claim 1, which is 2-(4-m-trifluoromethylphenylpiperazino)-ethyl 3,4,5-trimethoxybenzoate or its monohydrochloride.

4. A compound as claimed in claim 1, which is 2-(4-m-trifluoromethylphenylpiperazino)-ethyl 5-chloro-2-methoxy-benzoate or its monohydrochloride.

5. A compound as claimed in claim 1, which is 2-(4-m-trifluoromethylphenylpiperazino)-ethyl salicylate.

6. A compound as claimed in claim 1, which is 2-(4-m-trifluoromethylphenylpiperazino)-ethyl 2-acetoxybenzoate or its monohydrochloride.

7. A compound as clamed in claim 1, which is 2-(4-m-trifluoromethylphenylpiperazino)-ethyl anthranilate.

8. A compound as claimed in claim 1, which is 2-(4-m-trifluoromethylthiophenylpiperazino)-ethyl anthranilate.

* * * * *